United States Patent
Kim et al.

(10) Patent No.: US 12,096,911 B2
(45) Date of Patent: Sep. 24, 2024

(54) WINDOW SYSTEM FOR AN INTRAORAL SCANNER

(71) Applicant: SIRONA DENTAL SYSTEMS GMBH, Bensheim (DE)

(72) Inventors: Hong-Keun Kim, Frankfurt (DE); Martin Wohanka, Darmstadt (DE); Konrad Klein, Heidelberg (DE)

(73) Assignee: DENTSPLY SIRONA INC., York, PA (US)

(*) Notice: Subject to any disclaimer, the term of this patent is extended or adjusted under 35 U.S.C. 154(b) by 664 days.

(21) Appl. No.: 16/621,287

(22) PCT Filed: Jun. 14, 2018

(86) PCT No.: PCT/EP2018/065880
§ 371 (c)(1),
(2) Date: Dec. 11, 2019

(87) PCT Pub. No.: WO2018/229225
PCT Pub. Date: Dec. 20, 2018

(65) Prior Publication Data
US 2020/0163533 A1    May 28, 2020

(30) Foreign Application Priority Data

Jun. 14, 2017 (DE) ............... 10 2017 209 999.2

(51) Int. Cl.
*A61B 1/00* (2006.01)
*A61B 1/12* (2006.01)
(Continued)

(52) U.S. Cl.
CPC .......... *A61B 1/00096* (2013.01); *A61B 1/127* (2013.01); *A61B 1/128* (2013.01);
(Continued)

(58) Field of Classification Search
CPC ... A61B 1/00096; A61B 1/00142; A61B 1/24; A61B 1/127; A61B 1/128; A61B 1/253; A61L 31/026; A61C 19/04
(Continued)

(56) References Cited

U.S. PATENT DOCUMENTS 5,051,823 A * 9/1991 Cooper .................... A61C 1/08
348/66
5,354,977 A * 10/1994 Roustaei ............ G06K 7/10742
235/462.11
(Continued)

FOREIGN PATENT DOCUMENTS

| CN | 105796046 A | 7/2016 |
| CN | 106465483 A | 2/2017 |

(Continued)

OTHER PUBLICATIONS

International Search Report; PCT/EP2018/065880; Sep. 10, 2018 (completed); Sep. 19, 2018 (mailed).
(Continued)

*Primary Examiner* — Ricky D Shafer
(74) *Attorney, Agent, or Firm* — DENTSPLY SIRONA INC.

(57) ABSTRACT

The invention relates to a window system for an intraoral scanner. Said window system comprises an optical element having a thermal conductivity of more than $1\ W\ m^{-1}\ K^{-1}$. A window, which comprises a pane made for example of a plastic, glass, or corundum, is detachably disposed on the optical element at an average distance of less than 1 mm. At least one heat source is also connected to the optical element. The invention further relates to an intraoral scanner. Said intraoral scanner comprises the window system. The optical element and the at least one heat source are connected to the intraoral scanner. The window is disposed in a cover. Said cover can be disposed on the intraoral scanner (Continued)

such that the window has an average distance of less than 1 mm from the optical element.

10 Claims, 2 Drawing Sheets

(51) Int. Cl.
    *A61B 1/24*         (2006.01)
    *A61B 1/253*       (2006.01)
    *A61L 31/02*       (2006.01)

(52) U.S. Cl.
    CPC ............... *A61B 1/24* (2013.01); *A61B 1/253* (2013.01); *A61L 31/026* (2013.01); *A61B 1/00142* (2013.01)

(58) Field of Classification Search
    USPC .................................... 433/29; 359/507, 512
    See application file for complete search history.

(56) References Cited

U.S. PATENT DOCUMENTS

| | | | | |
|---|---|---|---|---|
| 5,471,326 A | * | 11/1995 | Hall | ................. G02B 26/106 |
| | | | | 359/18 |
| 5,536,236 A | | 7/1996 | Yabe | |
| 5,771,067 A | * | 6/1998 | Williams | ................ A61B 1/24 |
| | | | | 348/E5.025 |
| 7,221,522 B2 | * | 5/2007 | Tesar | ............... A61B 1/00096 |
| | | | | 359/833 |
| 7,262,484 B2 | * | 8/2007 | Dunn | ................ H01L 29/7371 |
| | | | | 257/E29.174 |
| 9,357,926 B2 | | 6/2016 | Hollenbeck | |
| 9,943,221 B2 | | 4/2018 | Erdmann | |
| 2002/0135694 A1 | * | 9/2002 | Williams | ............ A61B 1/0615 |
| | | | | 348/E5.025 |
| 2003/0107652 A1 | * | 6/2003 | Williams | ............ A61B 1/0684 |
| | | | | 348/E5.025 |
| 2010/0238279 A1 | * | 9/2010 | Thoms | ................. A61B 1/247 |
| | | | | 348/E7.085 |
| 2011/0028788 A1 | * | 2/2011 | Oral | ........................ A61B 5/01 |
| | | | | 600/182 |
| 2012/0034573 A1 | | 2/2012 | Erdmann | |
| 2014/0146142 A1 | * | 5/2014 | Duret | ................... A61B 5/065 |
| | | | | 348/46 |
| 2015/0018613 A1 | * | 1/2015 | Hollenbeck | ......... A61B 5/1076 |
| | | | | 600/109 |
| 2015/0238072 A1 | * | 8/2015 | Makmel | ........... A61B 1/00142 |
| | | | | 219/221 |
| 2016/0256245 A1 | * | 9/2016 | Van Der Poel | ........ A61B 1/053 |
| 2017/0340198 A1 | * | 11/2017 | Elazar | ...................... G06T 3/60 |

FOREIGN PATENT DOCUMENTS

| | | |
|---|---|---|
| DE | 202010017255 U1 | 6/2011 |
| EP | 2408347 B1 | 12/2014 |
| JP | H03118021 A | 5/1991 |

OTHER PUBLICATIONS

Written Opinion of the International Searching Authority; PCT/EP2018/065880; Sep. 10, 2018 (completed); Sep. 19, 2018 (mailed)
Patentability; PCT/EP2018/065880; Sep. 10, 2018 (completed); 19.
International Preliminary Report on Sep. 2018 (mailed).

* cited by examiner

WINDOW SYSTEM FOR AN INTRAORAL SCANNER

TECHNICAL FIELD

The present invention relates to a window system for an intraoral scanner. The invention further relates to an intraoral scanner comprising the window system.

BACKGROUND OF THE INVENTION

In the case of medical devices used intraorally or intracorporeally, the use of a housing creates a separation between the functional unit and the patient. Among other things, this prevents soiling or contamination of components inside the housing. However, the housing also serves to protect the user and the patient from mechanical, electrical, biological and chemical hazards. The housing must not interfere with the medical function. Therefore, in optical diagnostic devices and optical instruments used in therapy, the beam path pertinent to the function is ensured by openings of transparent windows or translucent windows.

The housing and its parts have to satisfy stringent requirements in terms of function and hygiene for single or multiple use, while at the same time being economical and suitable for everyday use. For repeated hygienic usability, the contact area between the patient and device must be able to be cleaned and disinfected or, if necessary, sterilized.

In the case of intraorally used 3D scanners that can measure the tooth topology, contact with the exhaled breath of the patient or the air in the oral cavity causes fogging if the surface temperature of a transparent window The formation of the condensate alters the light path. In the case of a 3-dimensional measurement, for example by means of fringe projection, triangulation, or confocal measurement, this can lead to significant erroneous data and/or to a too low data density.

Fogging of a transparent window can be prevented by a supply of cold or warm air. In sensitive patients, however, the flow of air may cause discomfort. The generation of an airflow also leads to increased power consumption and noise emissions. In addition, the nozzle required for this purpose takes up space on the intraoral scanner.

A dental diagnostic device, which comprises image acquisition means and has a window that is located in the beam path of the means for image acquisition, is known from DE 10 2009 013 615 A1. The window is made of quartz glass, sapphire or a plastic. A resistance heater is provided for heating the window.

It describes an intraorally used 3D scanner, the window of which is connected to a heater. The heater comprises an electromagnetic heat source.

An object of the present invention is to provide a window system for an intraoral scanner, as well as an intraoral scanner provided with said window system, that is protected against fogging even without generating an air flow and, in the case of repeated use, satisfies stringent hygienic requirements.

SUMMARY OF THE INVENTION

An optical element has a thermal conductivity of more than 1 W m$^{-1}$ K$^{-1}$, preferably more than 40 W m$^{-1}$ K$^{-1}$. A window comprises a pane made of plastic, glass, or corundum. It is detachably disposed on the optical element in such a way that a transfer of heat by means of thermal radiation, convection or thermal conduction is made possible, the result of which is a fog-reducing effect. The intermediate space between the optical element and the window can be void of air (vacuum), filled with a gas (air), or filled with a sticky or non-sticky liquid or solid, provided that it does not significantly affect the light path. Particularly preferably, the optical element is connected to the window. In this context, connected means that a surface of the optical element that is provided as a light path is in contact with a surface of the window that is likewise provided as a light path. In the case of perfectly flat surfaces, contact at the microscopic level is complete across the entire surface. In the current state of the art, however, the flatness of the surfaces is limited and there is contact only in some areas or locations. The window system further comprises at least one heat source that is connected to the optical element.

The optical element is in particular a window or a prism. Such a prism has a greater thermal capacity than a window and additionally causes a change in the optical beam path. For example, a deflection of the optical beam path by 90° can occur as a result of total internal reflection within the prism.

The window system can be attached to the intraoral scanner in such a way that the optical element faces a light source and/or a sensor of the intraoral scanner. The window then faces the oral cavity of a patient. Only the window is exposed to contamination from the oral cavity of the patient.

The material of the window is preferably selected from the group consisting of a polycarbonate (PC), a cycloolefin copolymer (COC, COP), a polymethyl methacrylate (PMMA), a float glass, a mineral glass or mixtures of these materials. These are materials that are highly transparent and satisfy the hygienic requirements for intraorally used medical devices, while at the same being so inexpensive that they are suitable for single use. Since the window is detachably connected to the optical element, it can be replaced by a new window after use of the intraoral scanner or treated hygienically. The window can be designed to either be rigid or as a flexible film.

Alternatively, the material of the window is a corundum, in particular sapphire glass. In this embodiment, the window is intended for multiple use.

Any fogging of the window system would take place on the window facing in the oral cavity of the patient. The invention provides for heating the window to prevent its surface temperature from falling below the dew point. In order to ensure the interchangeability of the window, however, the window itself is not equipped with a heat source. Instead, the at least one heat source is disposed on the optical element. For this purpose, the optical element preferably consists of a corundum. As a material of the optical element, corundum not only has a high optical quality, but also a high thermal conductivity. It can consequently absorb heat emitted by the at least one heat source and transfer it to the window over its entire surface. This allows the necessary heating of the window to be realized. Whereas a corundum, such as sapphire glass in particular, would be too expensive for single use, the fact that the optical element does not come into contact with the oral cavity of the patient, but is separated from it by the window, makes it possible to use this material in the window system according to the invention.

In a preferred embodiment of the window system, the heat source is a layer of ITO (indium tin oxide) disposed on the optical element. In one embodiment, said layer is located on the side of the optical element facing the window, so that heat can be transferred not only to the optical element, but also directly to the window. In another embodiment, the layer is located on the side of the optical element facing away from the window for reasons of electrical safety. An ITO layer is electrically conductive and transparent. If it is electrically contacted, it can generate heat through a current flow.

In order to mitigate a reduction in the transmittance of the window system by the presence of the ITO layer, it is particularly preferred that the ITO layer is adjusted to the refractive index of the optical element. Such an ITO layer is referred to as IMITO (index matched indium tin oxide).

Even an IMITO layer disposed over the entire surface of the optical element still causes a slight reduction in the transmittance of the window system compared to a window system that has no such layer. It is therefore further preferred that the ITO layer is disposed only in a peripheral region of the optical element. Peripheral region refers in particular to a region of the optical element, the width of which corresponds to at most 25 percent of the width of the optical element and the length of which corresponds to at most 25 percent of the length of the optical element. Due to the good thermal conductivity of the optical element, it is sufficient to heat said optical element by means of the ITO layer in the peripheral region, so that the heat is distributed evenly over the entire optical element and transferred from the optical element to the entire surface of the window. In this design of the ITO layer, the middle portion of the optical element that functions as the light path is not provided with an ITO layer, so that the transmittance of the window system is not impaired. A transmittance of more than 99 percent can thus be realized.

In another preferred embodiment of the window system, the heat source is configured to transfer waste heat from the intraoral scanner to a peripheral region of the optical element. Therefore, the heat source itself does not produce any heat. For this purpose, the heat source can in particular be disposed on an outer edge of the optical element. Just as when using an ITO layer in a peripheral region of the optical element, the window system in this embodiment is designed such that no part of the heat source is in the light path of the window system. In this embodiment too, the good thermal conductivity of the optical element allows the heat emitted by the heat source to first be transferred from the edge of the optical element over the entire surface of the optical element and then to the entire surface of the window. In comparison to a window system comprising an ITO layer, the window system according to this embodiment has the additional advantage that it can be manufactured in a simple manner. There is no need for electrical contact and supply of the necessary current, or induction coils for heating the ITO layer. Galvanic isolation and the avoidance of risk to the patient arising from the presence of additional electrical lines are not necessary either. Instead, it is enough to realize the heat source as a component made of a material that conducts heat well, in particular a metal, that is connected to heat-producing components in another area of the intraoral scanner.

However, the heat source for the optical element is not limited to the methods described above. Any conventional method of heat generation, such as an induction heater, a heating wire or a glued-on film, can be used.

In order to ensure a high quality of the data recorded by means of the intraoral scanner, it is preferred that the optical element has an anti-reflective coating on either side of its light path; in the case of a design as a window, on either side of its pane. It is further preferred that the window has an anti-reflective coating on either side of its pane as well. Normally, the use of such anti-reflective coatings in intraorally used medical devices poses problems, because they are attacked, soiled or clouded during autoclaving, as a result of which the optical quality of the coating is reduced. The coatings on the optical element in the window system are protected by the window, however, and therefore do not have to be autoclaved for sterilization. The optical element is furthermore protected from scratches, which can likewise cause an impairment of the 3D measurement and/or an impairment of the data quality.

Since the window can be designed as a disposable product, the anti-reflective layers applied to it can be disposed of together with the window.

In order to be able to detachably connect the window to the optical element and also ensure that no saliva, blood or other fluid from the oral cavity of a patient can pass the window and reach the optical element, it is preferred that the window is disposed in a cover for the intraoral scanner. In a preferred embodiment, this cover, which can also be referred to as a sleeve, is designed as a disposable product, just like the window. In this embodiment, it is permanently connected to the window and can be disposed of along with said window. For this purpose, it is designed as a cover consisting in particular of a silicone, latex, or a plastic film or a solid plastic, such as in particular an acrylonitrile styrene acrylate copolymer (ASA) or an acrylonitrile butadiene styrene copolymer (ABS). It can be designed to be hard or elastic. The cover comprises a window region in which the window is disposed. In order to ensure a liquid-tight connection, it can in particular be connected to the plastic cover by means of overmolding or adhesive bonding.

Even with a non-liquid-tight connection between the window and the cover, an increased protective effect against cross-contamination can be achieved with process-appropriate use, cleaning and disinfection.

In another preferred embodiment, the cover is reusable. For this purpose, it is autoclavable, so that it can be sterilized prior to reuse. Suitable materials for an autoclavable cover can be metals or plastics, whereby both hard and elastic plastics can be used. The window is designed to slide into a window region of the cover, so that it can be removed and disposed of after use of the cover. After autoclaving, the cover can then be fitted with a new window. This cover can, however, also in particular be equipped with a window made of corundum intended for multiple use.

An intraoral scanner comprising a window system, in which the window is disposed in a cover for the intraoral scanner, is designed such that the optical element and the at least one heat source are connected to the intraoral scanner. The cover is disposed on the intraoral scanner such that the window can be disposed at an average distance of less than 1 mm from the optical element.

BRIEF DESCRIPTION OF THE DRAWINGS

Design examples of the invention are shown in the drawings and explained in more detail in the following description.

DETAILED DESCRIPTION OF THE INVENTION

In one design example of the invention, an intraoral scanner 10 comprises a window region 11, in which a window system is disposed. The window system serves as a light path for a light beam emitted by a light source disposed in the intraoral scanner 10 and as a light path for a light beam reflected by a tooth in the oral cavity of a patient, which is reflected back onto a sensor inside the intraoral scanner 10. In the region in which it is inserted into the oral cavity of a patient, the intraoral scanner 10 comprises a cover 12. A window of the window system is a part of the cover 12, while another optical element of the window system is part of the intraoral scanner 10.

In a first design example of the cover, said cover is made of an elastic silicone, with which a window of the window system in the window region 11 is overmolded.

In a second design example of the cover 12, said cover is made of steel. In the window region 11, the cover comprises a sliding frame into which a window of the window system is inserted.

In a third design example of the cover 12, said cover is made of ASA, into which the window is inserted.

Figure 1:
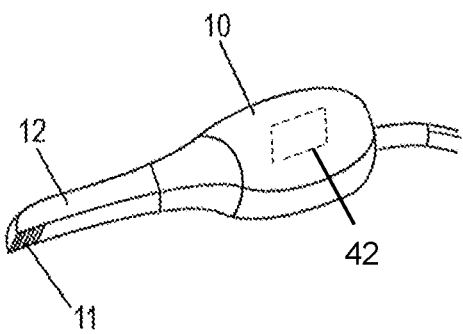
FIG. 1 shows an isometric illustration of an intraoral scanner according to a design example of the invention.
Figure 2:
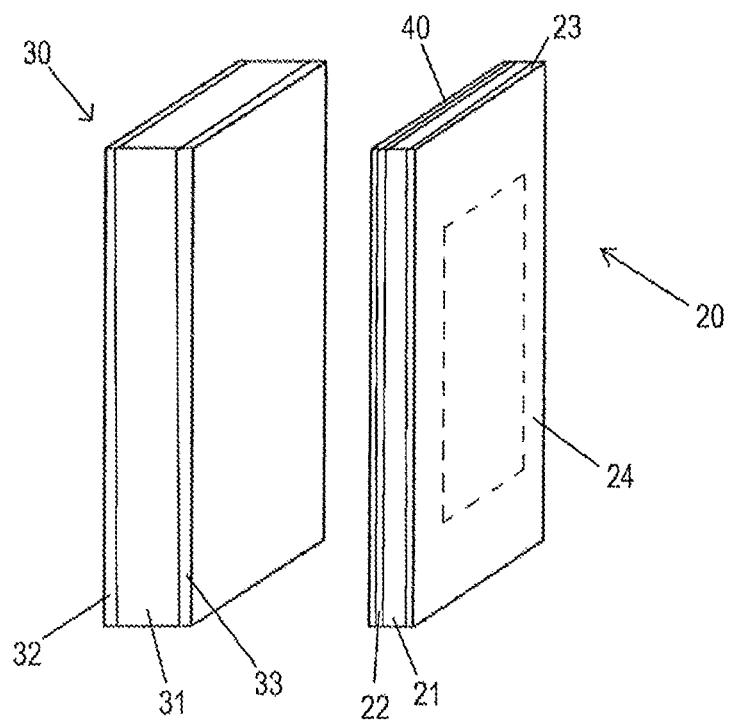
FIG. 2 shows an exploded view of a window system according to a design example of the invention.

FIG. 2 shows a first window 20 as an optical element and a second window 30 of a window system according to a first design example of the window system. The first window 20 is a part of the intraoral scanner 10, while the second window 30 is part of the cover 12. The first window 20 comprises a pane 21 made of a sapphire glass having a thermal conductivity of 41.9 W m$^{-1}$ K$^{-1}$. It is provided on both sides with an anti-reflective coating 22, 23 that covers the entire surface. In a peripheral region 24, which in FIG. 2 is separated from the rest of the first window 20 by a dotted line, on its side facing the second window 30, it comprises a heat source 40 in form of an ITO layer. It is electrically contacted such that it can be heated by an electric current flow or by induction. In the present design example, the second window 30 comprises a pane 31 made of polycarbonate, which is coated on both sides with an anti-reflective coating 32, 33 that covers the entire surface. When the cover 12 is pulled over the intraoral scanner 10, the second window 30 rests with one of its anti-reflective layers 33 on the first window 20 such that, in the peripheral region 24, it is in contact with the heat source 40 and, in the middle of the first window 20, it is in contact with one of the anti-reflective layers 22 thereof. The peripheral region 24 is not part of the light path, so that the heat source 40 does not impair the transmission of the light path. When the intraoral scanner 10 is in operation, the heat source 40 is switched on and heats both the first window 20 and the second window 30 in their respective peripheral regions. While the heat cannot initially be distributed uniformly in the second window 30 due to the poor thermal conductivity of polycarbonate, the good thermal conductivity of the sapphire glass brings about a uniform heating of the first window 20. The first window transfers the heat over its entire surface to the second window 30, so that, after a short time, the second window has a uniform temperature distribution as well.

In a second design example of the window system according to the invention, which is not depicted, the heat source 40 is not disposed on the side facing the second window 30, but rather on the side facing away from the second window 30.

Figure 3:
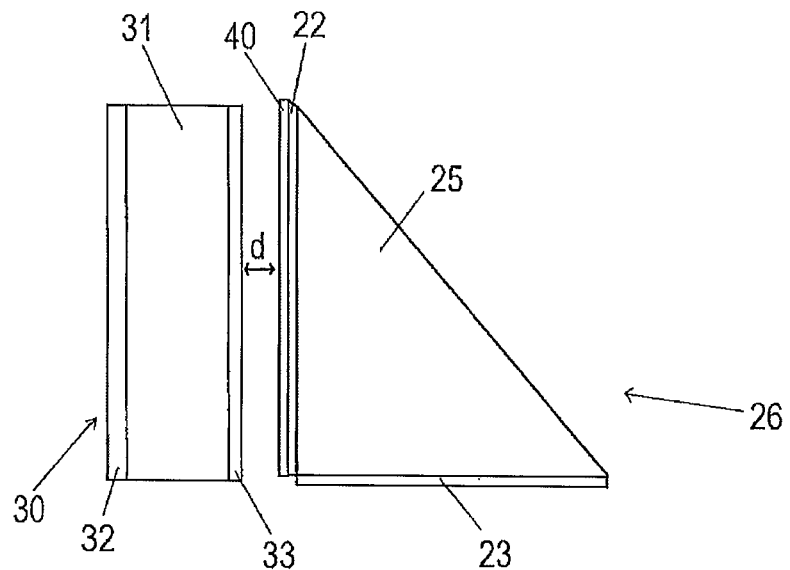
FIG. 3 shows a view onto a window system according to another design example of the invention.

A third design example of the window system according to the invention is shown in FIG. 3. This differs from the window system according to the first design example in that the optical element is designed as prism 26. It comprises a prism element 25, which is provided on both sides of its light path with an anti-reflective coating 22, 23 that covers the entire surface. On its side facing the second window 30, it has a heat source 40 in form of an ITO layer. The average distance d between the prism 26 and the second window 30 is 0.2 mm.

Figure 4:
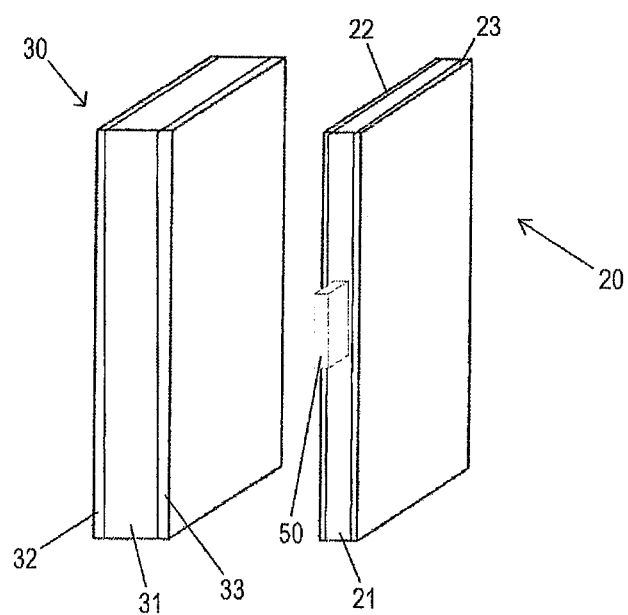
FIG. 4 shows an exploded view of a window system according to yet another design example of the invention.

A fourth design example of the window system according to the invention is shown in FIG. 4. This differs from the window system according to the first design example in that it does not comprise an ITO layer as a heat source 40. Instead, a heat source 50 is respectively disposed on the edges of the first window 20 and is connected to the heat generating components 42 of the intraoral scanner 10 in such a way the waste heat thereof is conducted to the edge of the first window 20. Even if, for ease of illustration, the heat source 50 in FIG. 4 is shown in such a way that it contacts only a portion of one edge of the first window 40, it is in fact designed as a frame that completely surrounds all four edges of the first window 20. During operation of the intraoral scanner 10, a variety of its components, such as its light source, heat up and conduct a portion of their waste heat to the edges of the first window 20 via the heat source 50. Due to its good thermal conductivity, the heat is distributed uniformly over the first window 20 and is then transferred from there to the entire surface of the second window 30.

After using the intraoral scanner 10, the cover 12 is removed from it. If the second window 30 is permanently connected to the cover 12, it is disposed of along with said cover. Otherwise, it is removed from the frame of the cover 12, the cover 12 is autoclaved and then provided with a new second window 30. This ensures that, the next time the intraoral scanner 10 is used, the entire area that comes into contact with the oral cavity of a patient is clean and sterile.

If the second window is not connected to the cover in a liquid-tight manner, use on the patient may require a set cleaning and disinfecting and/or sterilization procedure for the cover 12 in order to reduce the possibility of cross-contamination. In such a case, the cover 12 is removed from the intraoral scanner 10 after use and the second window 30 is disposed of.

If the second window 30 is connected to the cover 12 permanently but not in a liquid-tight manner, it is disposed of along with the cover and the intraoral scanner may require additional cleaning and/or disinfection and/or sterilization. This can be accomplished with a wipe-down disinfection, for example. For the next patient, a new, clean cover 12 has to be pulled onto the intraoral camera 10.

The invention claimed is:

1. A system, comprising;
   an intraoral scanner; and
   a detachable cover;
   the intraoral scanner further comprising an optical element having a thermal conductivity of more than 1 W m$^{-1}$ K$^{-1}$;
   at least one heat source disposed on a side of the optical element facing a window of the detachable cover, and
   the detachable cover further comprising the window that is part of the detachable cover, the window comprises a pane made of a plastic, glass, or corundum, and is configured to be an average distance (d) of less than 1 mm from the optical element when said detachable cover is attached to the intraoral scanner,
   wherein the optical element has an anti-reflective coating on either side of a light path of the optical element;
   wherein the at least one heat source is disposed on a periphery of the optical element, on a side facing the detachable cover such that the window of the detachable cover is in contact with the heat source, and wherein the at least one heat source is not part of a light path of the intraoral scanner, so that the at least one heat source does not impair the transmission of light in the light path;

wherein the at least one heat source is configured to heat both the optical element and the window of the detachable cover.

2. The system according to claim 1, wherein the optical element has a thermal conductivity of more than 40 W m$^{-1}$ K$^{-1}$.

3. The system according to claim 1, wherein the optical element is made of a corundum.

4. The system according to claim 1, wherein the average distance (d) between the optical element and the window is less than 0.5 mm.

5. The system according to claim 1, wherein the at least heat source is an ITO layer disposed on the optical element.

6. The system according to claim 5, wherein the ITO layer is an IMITO layer adjusted to the refractive index of the optical element.

7. The system according to claim 5, wherein the ITO layer is disposed only in a peripheral region of the optical element.

8. The system according to claim 1, wherein the window includes a material that is selected from the group consisting of a polycarbonate, a cycloolefin copolymer, a polyacrylmethacrylate, a float glass, a mineral glass, a corundum, and mixtures thereof.

9. The system according to claim 1, wherein the window is made of a corundum.

10. The system according to claim 1, wherein the window has an anti-reflective coating on either side of another pane of the window.

* * * * *

UNITED STATES PATENT AND TRADEMARK OFFICE
CERTIFICATE OF CORRECTION

| | | |
|---|---|---|
| PATENT NO. | : 12,096,911 B2 | Page 1 of 1 |
| APPLICATION NO. | : 16/621287 | |
| DATED | : September 24, 2024 | |
| INVENTOR(S) | : Kim et al. | |

It is certified that error appears in the above-identified patent and that said Letters Patent is hereby corrected as shown below:

On the Title Page

In item (71), in "Applicant", in Column 1, Lines 1-2, delete "SIRONA DENTAL SYSTEMS GMBH, Bensheim (DE)" and insert --DENTSPLY SIRONA INC., York, PA (US)-- therefor In the Claims In Column 6, Line 50, in Claim 1, delete "comprising;" and insert --comprising:-- therefor Signed and Sealed this
Eighteenth Day of March, 2025

Coke Morgan Stewart
*Acting Director of the United States Patent and Trademark Office*